US008211468B2

(12) United States Patent
Rozema et al.

(10) Patent No.: US 8,211,468 B2
(45) Date of Patent: *Jul. 3, 2012

(54) ENDOSOMOLYTIC POLYMERS

(75) Inventors: David B. Rozema, Middleton, WI (US);
Darren H. Wakefield, Fitchburg, WI (US); Jon A. Wolff, Madison, WI (US);
James E. Hagstrom, Middleton, WI (US); Kirk Ekena, Fitchburg, WI (US)

(73) Assignee: Arrowhead Madison Inc., Madison, WI (US)

( * ) Notice: Subject to any disclaimer, the term of this patent is extended or adjusted under 35 U.S.C. 154(b) by 1077 days.

This patent is subject to a terminal disclaimer.

(21) Appl. No.: 11/533,115

(22) Filed: Sep. 19, 2006

(65) Prior Publication Data

US 2007/0036865 A1    Feb. 15, 2007

Related U.S. Application Data

(60) Continuation-in-part of application No. 10/619,778, filed on Jul. 15, 2003, now Pat. No. 7,138,382, which is a division of application No. 09/589,978, filed on Jun. 7, 2000, now Pat. No. 6,630,351, and a continuation-in-part of application No. 10/816,081, filed on Apr. 1, 2004.

(60) Provisional application No. 60/137,859, filed on Jun. 7, 1999, provisional application No. 60/172,809, filed on Dec. 21, 1999, provisional application No. 60/460,455, filed on Apr. 4, 2003.

(51) Int. Cl.
*A61K 9/32* (2006.01)
*C07D 207/444* (2006.01)

(52) U.S. Cl. ...................... 424/486; 548/548

(58) Field of Classification Search .................. None
See application file for complete search history.

(56) References Cited

U.S. PATENT DOCUMENTS 5,140,013 A * 8/1992 Gaudreault et al. ....... 424/181.1
5,373,052 A * 12/1994 Fukuda et al. .............. 525/54.1

FOREIGN PATENT DOCUMENTS

WO    WO 9819710 A2 *    5/1998

OTHER PUBLICATIONS

Asayama S et al. "Synthesis of novel polyampholyte comb-type copolymers consisting of a poly(L-lysine) backbone and hyaluronic acid side chains for a DNA carrier." Bioconjug Chem. 1998; vol. 9 No. 4 pp. 476-481.
Blattler WA et al. "New heterobifunctional protein crosslinking reagent that forms an acid-labile link." Biochem. 1985; vol. 24 No. 6 pp. 1517-1524.
Boussif O et al. "A versatile vector for gene and oligonucleotide transfer into cells in culture and in vivo: polyethylenimine." Proc Natl Acad Sci USA. 1995; vol. 92 pp. 7297-7301.
Danko et al. "High expression of naked plasmid DNA in muscles of young rodents." Hum Mol Genetics. 1997; vol. 6 pp. 1435.
Dash PR et al. "Factors affecting blood clearance and in vivo distribution of polyelectrolyte complexes for gene delivery" Gene Ther. 1999; vol. 6 No. 4 pp. 643-650.
Dixon HBF et al. "Reversible Blocking of Amino Groups with Citraconic Anhydride." Biochem Journal. 1968; vol. 109 pp. 312-313.
Felgner PL et al. "Lipofection: A Highly Efficient, Lipid-Mediated DNA-Transfection Procedure." Proc Natl Acad Sci USA. 1987; vol. 84 pp. 7413-7417.
Futaki S. "Arginine-rich peptides: potential for intracellular delivery of macromolecules and the mystery of the translocation mechanisms." Int J Pharm. 2002; vol. 245 No. 1-2 pp. 1-7.
Garman AJ et al. "The Preparation and Properties of Novel Reversible Polymer-Protein Conjugates." FEBS Letters. 1987; vol. 223 No. 2 pp. 364-365.
Greenwald RB et al. "Poly(ethylene glycol) Conjugated Drugs and Prodrugs: A Comprehensive Review." Critical Reviews in Therapeutic Drug Carrier Systems. 2000; vol. 17 pp. 101-161.
Kamata H et al. "Amphiphilic peptides enhance the efficiency of liposome-mediated DNA transfection." Nucleic Acids Res. 1994; vol. 22 No. 3 pp. 536-537.
Kirby AJ et al. "Structure and Efficiency in Intramolecular and Enzymic Catalysis. Catalysis of Amide Hydrolysis by the Carboxy-group of Substituted Maleamic Acids." J Chem Soc Perkin. 1972; vol. 11 pp. 1206-1214.
Kircheis, R. et al. "Tumor targeting with surface-shielded ligand—polycation DNA complexes." J of Controlled Release. 2001; vol. 72 pp. 165-170.
Kishore K et al. "Polymers Containing Disulfide, Tetrasulfide, Diselenide and Ditelluride Linkages in the Main Chain." Advances in Polymer Sciences. 1995; vol. 12 pp. 83-92.
Kratz F et al. "Drug-polymer conjugates containing acid-cleavable bonds." Critical Reviews in Therapeutic Drug Carrier Systems. 1999; vol. 16 No. 3 pp. 245-288.
Lee HJ et al. "Pharmacokinetics and delivery of tat and tat-protein conjugates to tissues in vivo." Bioconjug Chem. 2001; vol. 12 pp. 995-999.
Legendre JY, et al. "Delivery of plasmid DNA into mammalian cell lines using pH-sensitive liposomes: Comparison with cationic liposomes." Pharmaceut. Res. 1992; vol. 9 pp. 1235-1242.
Lindgren M et al. "Cell-penetrating peptides." Trends Pharmacol Sci. 2000; vol. 21 pp. 99-103.
Mechtler K et al. "Gene transfer mediated by influenza virus peptides: the role of peptide sequences." New J Chem. 1997; vol. 21 pp. 105-111.
Meyer O et al. "Copolymers of N-isopropylacrylamide can trigger pH sensitivity to stable liposomes." FEBS Letters. 1998; vol. 421 pp. 61-64.

(Continued)

*Primary Examiner* — Jennifer Dunston
(74) *Attorney, Agent, or Firm* — Kirk Ekena (57) ABSTRACT

We describe pH-sensitive endosomolytic polymers, delivery particles containing pH-sensitive endosomolytic polymers. The described particles are capable of delivering polynucleotides to cells from the peripheral circulation with subsequent release from endosomes. The endosomolytic polymers are inactive outside the cell but disrupt membranes upon exposure to an acidified endosomal compartment.

2 Claims, 3 Drawing Sheets

OTHER PUBLICATIONS

Mukherjee S et al. "Endocytosis." Physiological Reviews. 1997; vol. 77 No. 3 pp. 759-803.

Murthy et al. "Design and synthesis of pH-responsive polymeric carriers that target uptake and enhance the intracellular delivery of oligonucleotides." J of Controlled Release. 2003; vol. 89 No. 30 pp. 365-374.

Murthy N. et al. "The design and synthesis of polymers for eukaryotic membrane disruption." J Controlled Release. 1999; vol. 61 pp. 137-143.

Murthy, N. et al. "Bioinspired pH-responsive polymers for the intracellular delivery of biomolecular drugs." Bioconjug Chem. 2003; vol. 14 No. 2 pp. 412-419.

Naganawa A et al. "Synthetic Studies on Tautomycin Synthesis of 2,3-Disubstituted Maleic-Anhydride Segment." Tetrahedron. 1994; vol. 50 No. 30 pp. 8969-8982.

Netz RR et al. "Complexation Behavior of Polyampholytes and Charged Objects." Macromolecules. 1998; vol. 31 No. 15 pp. 5123-5141.

Nieto MA et al. "Effects of Temperature and pH on the Regeneration of the Amino Groups of Ovalbumin After Modification with Citraconic and Dimethylmaleic Anhydrides." Biochimica et Biophysica Acta. 1983; vol. 749 pp. 204-210.

Nishikubo T et al. "Degradation of Dehydrochlorinated Poly(epichlorohydrin) Using Photo-Generated Cationic Catalysts." J of Polymer Science. 1986; vol. 24 pp. 1097-1108.

O'Brien-Simpson NM et al. "Polymerization of Unprotected Synthetic Peptides: A View Toward Synthetic Peptide Vaccines." J Am Chem. Soc. 1997; vol. 119 pp. 1183-1188.

Ogris M et al. "PEGylated DNA/transferrin-PEI complexes: reduced interaction with blood components, extended circulation in blood and potential for systemic gene delivery." Gene Ther. 1999; vol. 6 No. 4 pp. 595-605.

Ohmori N et al. "The enhancing effect of anionic alpha-helical peptide on cationic peptide-mediating transfection systems." Biochem Biophys Res Commun. 1997; vol. 235 No. 3 pp. 726-729.

Plank et al. "Activation of the complement system by synthetic DNA complexes: a potential barrier for intravenous gene delivery." Hum Gene Ther. 1996; vol. 7 No. 12 pp. 1437-1446.

Reddy JA et al. "Enhanced folate receptor mediated gene therapy using a novel pH-sensitive lipid formulation." J of Controlled Release. 2000; vol. 64 No. 1-3 pp. 27-37.

Remy JS et al. "Gene Transfer With a Series of Lipophilic DNA-Binding Molecules." Bioconjug Chem. 1994; vol. 5 pp. 647-654.

Ross PC et al. "Lipoplex size is a major determinant of in vitro lipofection efficiency." Gene Ther. 1999; vol. 6 pp. 651-659.

Rozema, D. B. et al. "Endosomolysis by Masking of a Membrane-Active Agent (EMMA) for Cytoplasmic Release of Macromolecules." Bioconjug Chem. 2003; vol. 14. pp. 51-57.

Schwarze SR et al. "In vivo protein transduction: delivery of a biologically active protein into the mouse." Science. 1999; vol. 285 pp. 1569-1572.

Senior JH et al. "Interaction of Positively-Charged Liposomes with Blood: Implications for Their Application In Vivo." Biochemica et Biophysica Acta. 1991; vol. 1070 No. 1 pp. 173-179.

Sezaki H et al. "Soluble macromolecular carriers for the delivery of antitumour drugs." Adv Drug Deliv Rev. 1989; vol. 3 No. 2 pp. 247-266.

Shah D et al. "Transcellular delivery of an insulin-transferrin conjugate in enterocyte-like Caco-2 cells." J Pham Sci. 1996; vol. 85 No. 12 pp. 1306-1311.

Sitaram N et al. "Interaction of Antimicrobial Peptides with Biological and Model Membranes: Structural and Charge Requirements for Activity." Biochimica et Biophysica Acta. 1999; vol. 1462 pp. 29-54.

Thorpe PE et al. "Comparison of Two Anti-Thy 1.1-Abrin A-Chain Immunotoxins Prepared With Different Cross-Linking Agents: Antitumor Effects, In Vivo Fate, and Tumor Cell Mutants." JNCI. 1987; vol. 79 No. 5 pp. 1101-1111.

Van de Wetering P et al. "Copolymers of 2-(Dimethylamino)Ethyl Methacrylate with Ethoxytriethylene Glycol Methacrylate of N-Vinyl-Pyrrolidone as Gene Transfer Agents." J of Controlled Release. 2000; vol. 64 pp. 193-203.

Vitiello L et al. "Transfection of Cultured Myoblasts in High Serum Concentration with DODAC:DOPE Liposomes." Gene Ther. 1998; vol. 5 No. 10 pp. 1306-1313.

Wagner E et al. "Influenza virus hemagglutinin HA-2 N-terminal fusogenic peptides augment gene transfer by transferrin-polylysine-DNA complexes: toward a synthetic virus-like gene-transfer vehicle." Proc Natl Acad Sci U S A. 1992; vol. 89 No. 17 pp. 7934-7938.

Wagner E et al. "Delivery of drugs, proteins and genes into cells using transferrin as a ligand for receptor-mediated endocytosis." Advanced Drug Delivery Reviews. 1994; vol. 14 pp. 113-135.

Wolfert MA et al. "Characterization of Vectors for Gene Therapy Formed by Self-Assembly of DNA with Synthetic Block Co-Polymers." Hum Gene Ther. 1996; vol. 7 pp. 2123-2133.

Woodle, M. C. et al. "Sterically stabilized liposomes" Biochimica et Biophysica Acta. 1992; vol. 1113 pp. 171-199.

Xu Y et al. "Mechanism of DNA release from cationic liposome/DNA complexes used in cell transfection." Biochem. 1996; vol. 35 No. 18 pp. 5616-5623.

Zauner W et al. "Rhinovirus-Mediated Endosomal Release of Transfection Complexes." J of Virology. 1995; vol. 69 No. 2 pp. 1085-1092.

Zhou X et al. "DNA Transfection Mediated by Cationic Liposomes Containing Lipopolylysine: Characterization and Mechanism of Action." Biochemica et Biophysica Acta. 1994; vol. 1189 No. 2 pp. 195-203.

Zhou X et al. "Lipophilic Polylysines Mediate Efficient DNA Transfection in Mammalian Cells." Biochemica et Biophysica Acta. 1991; vol. 1065 pp. 8-14.

* cited by examiner

```
SEQUENCE LISTING

<160> NUMBER OF SEQ ID NOS: 1

<210> SEQ ID NO 1
<211> LENGTH: 25
<212> TYPE: DNA
<213> ORGANISM: Photinus pyralis

<400> SEQUENCE: 1
cctcttacct cagttacaat ttata                                25
```

ENDOSOMOLYTIC POLYMERS

CROSS-REFERENCE TO RELATED APPLICATIONS

This application is a continuation-in-part of application Ser. No. 10/619,778, filed Jul. 15, 2003, issued as U.S. Pat. No. 7,138,382, which is a divisional of application Ser. No. 09/589,978 filed on Jun. 7, 2000, issued as U.S. Pat. No. 6,630,351, and a continuation-in-part of application Ser. No. 10/816,081, filed Apr. 1, 2004, pending, application Ser. No. 09/589,978 claims the benefit of U.S. Provisional Application No. 60/137,859, filed Jun. 7, 1999 and U.S. Provisional Application No. 60/172,809, filed Dec. 21, 1999, and application Ser. No. 10/816,081 claims the benefit of U.S. Provisional Application No. 60/460,455, filed Apr. 4, 2003.

BACKGROUND OF THE INVENTION

The current paradigm for the development of non-viral DNA delivery vectors is to model viral assembly and gene transfer by incorporating, in combinatorial fashion, functional groups that enable particular assembly and transfer steps. Cationic polymers or lipids are used to condense DNA into small virus-like particles. This condensation step is deemed important for several reasons: a) protection of the DNA from inactivation by blood components, b) protection of the DNA from degradation by extracellular nucleases, c) extravascularization of the particle across small openings (fenestrae) in endothelial barriers (for intravascular administration routes), and d) cellular endocytosis. Functional groups are incorporated into synthetic vectors to enhance cell targeting, endosomal escape, and nuclear targeting of the DNA to be delivered. These signals include cell-surface ligands designed to direct the vector to a particular cell type and/or enhance adsorptive or receptor-mediated endocytic uptake of the particle. The vector may also contain molecules designed to enhance release of endocytosed DNA particle into the cell cytoplasm. While the components of a DNA delivery vehicle are known in theory, forming an efficient non-viral delivery vector in practice has been problematic. Cationic polymers or lipids which are good at condensing DNA tend to be toxic or have poor biodistribution. Similarly, compounds which may possess good endosome disruption activity are also frequently toxic.

While cationic polymers and lipids are essential to condense DNA into nanoparticles, their cationic nature limits their wider utility for in vivo applications not only by low gene expression but by toxicity as well. The intravascular route of administration, an attractive approach for wide spread delivery, is particularly plagued by toxicity as well as biodistribution problems. Decreased transfection efficiency in vivo is due in part to the interaction of the polyplexes or lipoplexes with blood components such as serum proteins which inhibit transfection. This effect is usually attributed to the opsonization of the DNA complexes by serum components. Furthermore, intravenously-injected cationic DNA complexes also encounter unintended cell types such as macrophages, monocytes, neutrophils, platelets and erythrocytes, which are important potential mediators of toxicity. Toxic manifestations of systemically-administered cationic DNA complexes can range from red blood cell agglutination to potent inflammatory reaction and elevated serum levels of liver enzymes. Several studies have attempted to avoid such adverse interactions by including polyethyleneglycol (PEG) or proteins such as albumin or transferrin in the DNA complexes. Another method proposed to decrease the charge of a polycation-condensed DNA particle and thus decrease interaction with serum components is to recharge the DNA/polycation complex by addition of a polyanion. Alternating complexes of polycations and polyanions form layered structures when absorbed on macrosurfaces from aqueous solutions. It has been demonstrated that a similar phenomenon takes place on the surface of polycation-condensed DNA particles when they are further complexed with a third-layer polyanion (U.S. application Ser. No. 09/328,975, incorporated herein by reference).

The liver is one of the most important target tissues for gene therapy given its central role in metabolism (e.g., lipoprotein metabolism in various hypercholesterolemias) and the secretion of circulating proteins (e.g., clotting factors in hemophilia). At least one hundred different genetic disorders could be at least partially corrected by liver-directed gene therapy. Their cumulative frequency is approximately one percent of all births. In addition, acquired disorders such as chronic hepatitis and cirrhosis are common and could also be treated by polynucleotide-based liver therapies. Gene therapies involving heterotopic gene expression would further enlarge the number of disorders treatable by liver-directed gene transfer. For example, diabetes mellitus could be treated by expressing the insulin gene within hepatocytes whose physiology may enable glucose-regulated insulin secretion. Gene therapy encompassed the purposeful delivery of genetic material to cells for the purpose of treating disease as well as for biomedical investigation or research. Research can be used to study gene function or to facilitate drug discovery or validation.

While viral vectors are the basis of most pre-clinical studies and human clinical trials for delivery of DNA to liver cells, non-viral approaches are continuing to advance. Polyplexes, lipoplexes and lipopolyplexes have all been proposed for delivery vectors to the liver. Most liver non-viral transfer studies have used polyplexes typically containing poly-L-lysine or PEI and ligands for the asialoglycoprotein receptor (ASGPr). Liposomes and lipopolyplexes for liver gene transfer have been reported as well. We are focused on developing DNA nanoparticles that are better at traversing two critical steps: passing through the circulatory system to gain access to hepatocytes and releasing their genetic cargo from the endosomes. The particles may contain ligands to enhance hepatocyte targeting and uptake.

SUMMARY OF THE INVENTION

Described herein are pH-labile reversibly modified polymers, polynucleotide delivery particles containing said polymers and methods for generating said polymers and particles. The described particles incorporate endosomolytic chemistries and nanotechnologies to assemble nanoparticles capable of delivering polynucleotides to cells from the peripheral circulation with subsequent release from endosomes.

In a preferred embodiment, we describe compounds and particles incorporating said compounds to release molecules from an endosome to the cytoplasm in a cell. The compounds comprise reversibly inhibited membrane active polymers which undergo selective chemical cleavage events in the acidic environment of the endosome. Prior to entering the endosome, activity of the membrane active polymer is suppressed by the reversible covalent attachment of an inhibitor. Upon exposure to acidic conditions, such as in an acidified endosome or lysosome, the bond linking the inhibitor to the polymer is broken, unmasking the membrane activity of the polymer.

In a preferred embodiment, we describe nanoparticles for delivering a polynucleotide to a cell. The particles comprise a polyanion ionically associated with a polynucleotide/polycation binary complex. The polycation, the polyanion or both consist of a membrane active polymer. A membrane active polycation may be reversible inhibited. The polyanion can be a reversibly modified membrane active polyamine. The polyanion recharges the complex to reduce the positive charge of the binary complex or to increase the negative charge of the nanoparticle. The nanoparticle can be positively charged, negatively charged, or charge neutral. The particle can contain a plurality of polynucleotides, polycations or polyanions. To increase stability of the particle, polycations and polyanions of molecular weight greater than about 10,000 daltons are preferred. Stability of the particles can be further increased by crosslinking the polyanion to the polycation.

In a preferred embodiment are described methods for forming transfection competent nanoparticles comprising: condensing a polynucleotide with a polycation to form a binary complex and recharging the binary complex by addition of a polyanion to form small (<150 nm), stable, negatively-charged polynucleotide-containing ternary complex. The polycation, the polyanion or both consist of membrane active polymers. A membrane active polycation may be reversible inhibited. The polyanion can be a reversibly modified/inhibited membrane active polymer. The particle can contain a plurality of polynucleotides, polycations or polyanions. To increase stability of the particle, polycations and polyanions of molecular weight greater that about 10,000 daltons are preferred. Stability of the particles can be further increased by crosslinking the polyanion to the polycation.

In a preferred embodiment is described a method for delivering a molecule to the cytoplasm of the cell comprising: associating the molecule with a reversibly inhibited membrane active polymer to form a complex and delivering the complex to the cell wherein the complex is endocytosed. Prior to entering the endosome, the membrane activity of the polymer is masked by the covalent attachment of an inhibitor. Selective chemical cleavage of the inhibitor(s) from the membrane active polymer occurs in the acidic environment of the endosome, restoring activity of the polymer. Disruption of the endosomal membrane then facilitates release of the molecule into the cytoplasm of the cell. Endosomal release is of importance for the delivery of a wide variety of molecules that are incapable of diffusion across cellular membranes.

In a preferred embodiment we describe large acid-cleavable polyanions that have potent endosomolytic activity and that can recharge cationic polynucleotide-containing complexes and methods for synthesizing the large acid-cleavable polyanions. The negatively-charged nanoparticles are small and stable in physiological saline and possess transfection activity.

Further objects, features, and advantages of the invention will be apparent from the following detailed description when taken in conjunction with the accompanying drawings.

DETAILED DESCRIPTION

We have developed a strategy for endosomal release of membrane impermeable molecules. This strategy involves the reversible inactivation of a membrane active or membrane lysing agent. The reversible inactivation of the membrane active agent is accomplished by attaching an inhibitor or plurality of inhibitors to the membrane active agent by a bond or plurality of bonds that cleave in the environment of an endosome. The inhibitor prevents the agent from lysing the cytoplasmic membrane and thereby causing cell death. The inhibitor is removed from the agent in the acidic environment of the endosome by cleavage of a labile bond, thereby allowing the membrane active agent to disrupt the endosomal membrane to effect release of endosomal contents into the cytoplasm.

A key component to limiting membrane activity to the endosome is the labile bond, which must be stable under extracellular conditions, but very unstable in the endosomal vesicle. In particular, we have focused on the identification of bonds that are cleaved in an acidic environment. Acidification is a characteristic of the endosome environment that is commonly exploited by viral and non-viral delivery vehicles. Agents which rely on protonation to become membrane active, such as polypropylacrylic acid and peptide derivatives of the viral coat protein hemagluttinin, have a serious flaw. Activation of the agent causes partial disruption of the endosome, thus destroying the pH gradient and leading to inactivation of the membrane active agent. This cycle can limit the effectiveness of the membrane active agent in delivery of macromolecules to the cell cytoplasm. In contrast, the invention as described herein, results in essentially irreversible reactivation on membrane active agents upon exposure to an acidic pH environment.

An important consideration in selecting labile bonds for use in cellular delivery systems is the kinetics of bond cleavage upon exposure of the bond to acidic pH. The kinetics of endosome acidification and maturation of the endosome to a lysosome are very rapid compared to the rates of cleavage for most of the acid-labile bonds reported in the literature. Once endocytosis occurs, the pH drops from the extracellular pH (about 7.4) to pH about 5 in roughly 10 min. Endosomal contents are quickly exposed to active lysosomal enzymes and degradation of the molecule to be delivered may occur. Therefore, bonds that are cleaved in within minutes in the pH range 5-7 are preferred.

Figure 1:
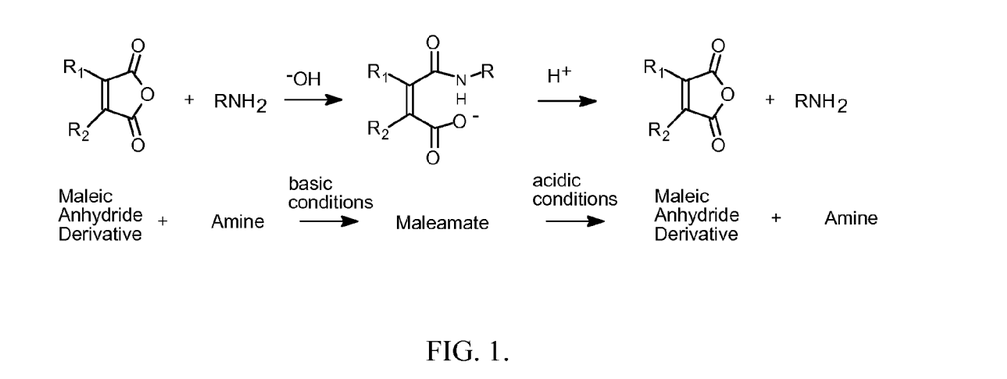
FIG. 1. Illustration of pH-labile reversible chemical modification of an amine-containing molecule with a maleic anhydride derivative to form a maleamate following by acid cleavage of the modification. For monosubstituted maleic anhydrides, $R_1$ or $R_2$ is a hydrogen and $R_2$ or $R_1$ is linked to the anhydride via a carbon-carbon bond. For a disubstituted maleic anhydrides both $R_1$ and $R_2$ are linked to the anhydride via carbon-carbon bonds.
Figure 2:
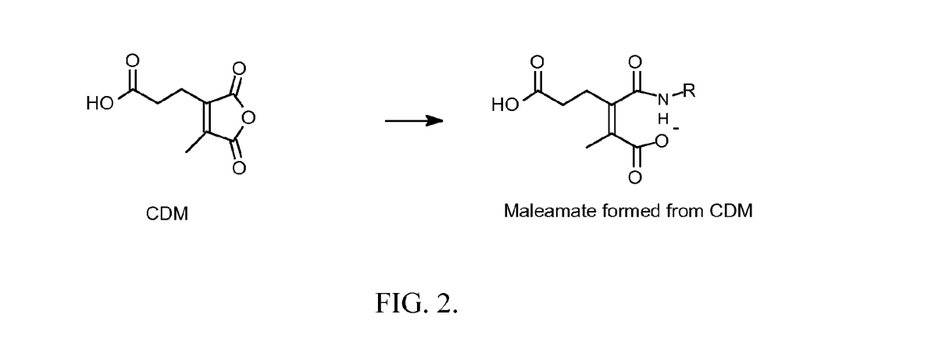
FIG. 2 Illustration of pH-labile reversible chemical modification of an amine-containing molecule with the disubstituted maleic anhydride derivative CDM (2-Propionic-3-Methylmaleic Anhydride).

A well-studied pH-labile bond is the maleamate bond, which is derived from the reaction of an amine and a maleic anhydride or maleic anhydride derivative (FIG. 1). The rate of maleamate cleavage is dependent upon the structure of the maleic anhydride used to form the maleamate. In general, disubstituted maleamates are more labile than monosubstituted maleamates, which are more labile than unsubstituted maleamates. The monosubstituted maleamates are the most studied members of this family, and have half-lives of hours at pH <5. According to literature, disubstitution of the maleamate results in about two orders of magnitude increase in the rate of cleavage. We have found that the disubstituted maleamate bond derived from dimethylmaleic anhydride ($R_1$ and $R_2$=$CH_3$ in FIG. 1) has a half-life of about 2 min at pH 5. This rate is on the same order as endosome maturation. In contrast, we have found that monosubstituted maleamate bonds derived from methylmaleic anhydride ($R_{1or2}$=H and $R_{2or1}$=$CH_3$ in FIG. 1) have a half-life of cleavage of about 300 min (5 hours) at pH 5. To increase charge and solubility, derivatives of dimethyl maleic anhydrides, such as 2-Propionic-3-Methylmaleic Anhydride ((Naganawa et al. 1994; Carboxylated DimethylMaleic anhydride or CDM) may be used (FIG. 2).

The ability of a disubstituted maleic anhydride to reversibly inhibit membrane activity of the peptide melittin until reaching the acidic environment of the endosome was reported by us (Rozema et al. 2003). We demonstrated the ability of the reversibly inhibited melittin to deliver the membrane impermeable molecules polyethyleneglycol and an oligonucleotide to the cell cytoplasm. In these examples of delivery, the delivery reagent (CDM-modified melittin) and compound were not connected or associated with each other, but independently delivered to common endocytic compartments in the cell. For delivery of membrane impermeable molecules to the cytoplasm of cells in vivo, there must be an association between the molecule and the delivery agent. We now provide membrane active agents that may be noncovalently associated with or covalently linked to the membrane impermeable molecule for delivery of the molecule to the cytoplasm of a cell.

Recharging of DNA Particles:

DNA can be condensed with an excess of polycation in aqueous solutions to form nanoparticles with positive surface charge. This phenomenon is critical not only to chromatin and viral assembly, but also is important in the construction of gene delivery vehicles. The positive charge surplus contained in polycation-condensed DNA complex can be used to deposit a layer of polyanions on the surface DNA/polycation complex resulting in negatively charge particles (or complexes) in a process termed recharging (U.S. patent application Ser. No. 09/328,975). Negatively charged particles may reduce nonspecific interactions that cationic particles have with serum proteins, cell surfaces, and the extracellular matrix. Recharging is a two-step process. In step one, the DNA or other polynucleotide is condensed by addition of an excess of polycation to form a positively-charged polynucleotide nanoparticle. Typical polynucleotide delivery formulations stop at this point and add the nanoparticle to the cell. In the recharging process, a third polyion (a polyanion) is added to the positively-charged polycation/polynucleotide particle to make a ternary complex that has a neutral to negative surface charge. Under proper formulation conditions, the particles are small (<150 nm), and are termed nanoparticles.

Negatively charged complexes should be better able to circulate and target specific cells in vivo by reducing non-specific interactions with negatively charged cells surfaces, serum proteins, and the extracellular matrix.

Figure 3:
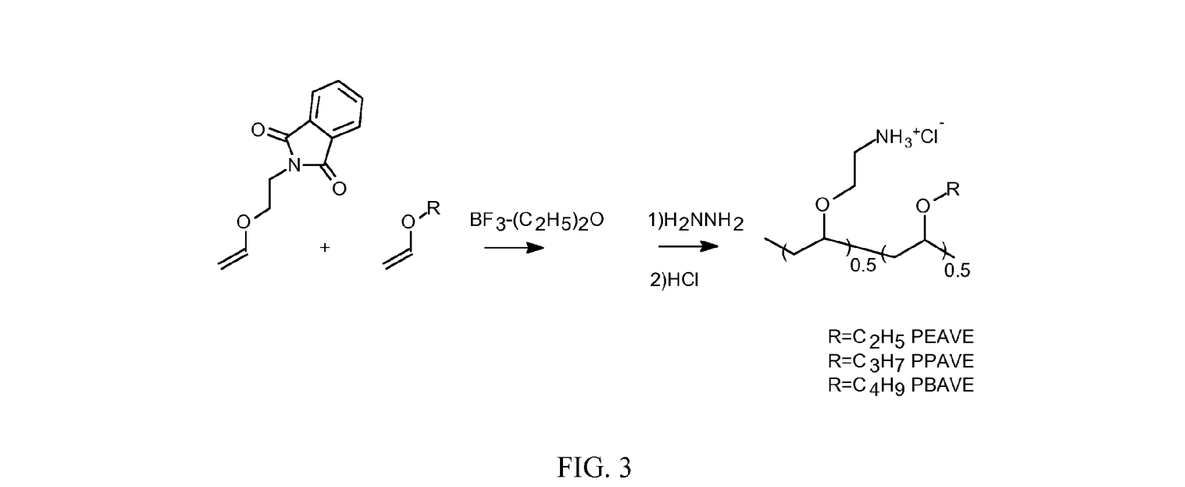
FIG. 3 Illustration of the synthesis of amphiphilic polyvinylether polycations.

Membrane Active Polymers for Polynucleotide Particle Formulation:

In order for the reversibly-masked membrane active agent to facilitate the delivery polynucleotides or other membrane impermeable molecules to cells, the masked membrane active agent must be associated with the molecule. Small membrane active agents with low overall charge, such as the membrane lytic peptide melittin, can form particles with polynucleotides. However, these particles are large (>150 nm) and unstable (i.e., they increase in size in the presence of physiological concentrations of salt). Larger membrane active polymers can be used to form small, stable particles with polynucleotides. We have previously synthesized membrane active polymers composed of amines and alkyl groups via copolymerization of various alkyl vinyl ethers with an amine-protected monomer (amphiphilic polyvinylether polycations; FIG. 3 and U.S. patent application Ser. No. 10/772, 502, incorporated herein by reference). As an example, a 50:50 mixture of alkyl groups and amines yields polymers containing ethyl (PEAVE), propyl (PPAVE), and butyl (PBAVE) groups using trifluoride etherate as an initiator. Deprotection of the amine-protecting phthalimide groups results in water soluble polymers with molecular weight about 20,000 Daltons.

Figure 4:
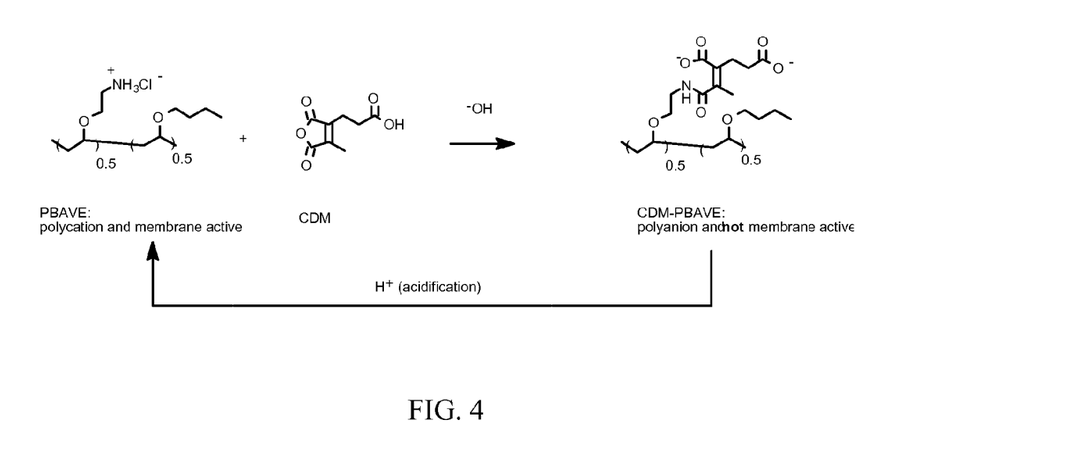
FIG. 4. Illustration of reversible masking of membrane activity of the PBAVE polymer through pH-labile attachment of inhibitors to the polymer.

The butyl-containing polymer PBAVE was found to be about 60% as hemolytic as melittin when assayed for red blood cell lytic activity. Reversible inhibition of PBAVE can be accomplished by CDM modification. Incubation of the modified polymer at pH 5 restored lytic ability with a half-life of about 10 min. Therefore, the membrane activity of the polymer PBAVE can be controlled by modification of the polymer with CDM. Under basic conditions the polymer is not membrane lytic. Upon acidification, the CDM inhibitor is cleaved from the polymer and membrane activity of the polymer is restored (FIG. 4). The endosomolytic activity of CDM-PBAVE is demonstrated by its ability to deliver a polynucleotide to cells (see example 5 below). CDM and CDM derivatives can be used to modify any amine-containing membrane active polymer.

Recharging of Nanoparticles with Reversibly Inhibited Membrane Active Polymers:

In addition to masking the membrane activity of an amine-containing polymer, modification of a polymer with the CDM maleic anhydride derivative further reversibly converts positive charges on the polymer to negatively charged carboxyl groups. Thus, a polycation can be converted to a polyanion. Following condensation of a polynucleotide with a first polycation to form a small binary complex or particle, a polyanion may then be used to recharge the binary complex and form a ternary complex or particle which has a less positive or more negative surface charge than the binary complex. In recharging a polynucleotide-containing particle with a CDM-modified second polycation, the recharging layer is acid-labile. Exposure of this recharged nanoparticle to acidic conditions results in cleavage of the CDM groups from the polyanion with concomitant loss of negative charge from the recharging polymer. Reversion of the polyanion to a membrane active polycation (second polycation) can have several effects including: destabilization of the particle, release of membrane active agent in the endocytic vesicle, and increased interaction of the first polycation with the endocytic vesicle membrane. The first polycation can also be a membrane active polymer and may further be of the same species as the membrane active second polycation. Disruption of the endosome by the membrane active polymer(s) results in cytoplasmic delivery of the polynucleotide or other molecule present originally present in the recharged particle.

Transfection with Small, Negatively-Charged, Acid-Labile Nanoparticles:

We have shown that endosomolysis can be achieved by reversibly modifying a membrane active peptide such as melittin with maleic anhydride derivatives (Rozema et al. 2003; U.S. patent application Ser. No. 10/444,662). CDM-melittin's ability to delivery macromolecules polyethylene glycol and an uncharged oligonucleotide analog has been shown. However, in order to incorporate masked membrane active agents into polynucleotide-delivery vectors we synthesized polymers of sufficient size and charge to be formulated into stable polynucleotide-containing nanoparticles. As an example, the polycation PBAVE was synthesized and demonstrated to have both membrane activity and the ability to form small, stable particles with DNA. Masking of PBAVE's membrane activity by reaction with CDM resulted in a polyanion that can be used to recharge DNA/polycation particles to make small, negatively-charged, acid-labile nanoparticles.

Nanoparticles composed of DNA:PBAVE:CDM-PBAVE were formulated at a 10:20:80 weight ratio and applied to cultured mouse liver cells (Hepa-1clc7) in tissue culture in the presence of DMEM and 10% serum. The DNA used in the delivery formulations was pCILuc, which contains a gene encoding luciferase. The transfection ability of the complexes was determined by measuring the relative light units of luciferase produced by cells that had been treated with pCI-Luc-containing nanoparticles. As a control for the reversibly inhibited membrane active polymer (CDM-PBAVE), particles were also constructed using succinylated-PBAVE (S-PBAVE) and cis-aconitylated-PBAVE (A-PBAVE). cis-Aconitic anhydride is a monosubstituted maleic anhydride derivative that has a carboxylate ($CH_2CO_2H$) substituent on the maleic anhydride. Succinylation is irreversible and cis-aconitylation cleaves with a half-life of about 300 min at pH 5.

There is a dependence of transfection on the liability of the group used to modify/inhibit the membrane active agent PBAVE. The reversibly-masked, membrane active polymers CDM-PBAVE and A-PBAVE were able to transfect cells while the irreversibly modified polymer (S-PBAVE) was inactive. In addition, the nanoparticles containing CDM-PBAVE (disubstituted maleamate bonds) had 30-fold more transfection activity than nanoparticles formed with A-PBAVE (monosubstituted maleamate bonds). The increase in transfection ability of the CDM-PBAVE containing particles is most likely related to the greater lability of the CDM disubstituted maleic anhydride derivative relative to the cis-aconitic monosubstituted maleic anhydride derivative. Similar results are expected for other amine-containing membrane active polymers.

Figure 5:
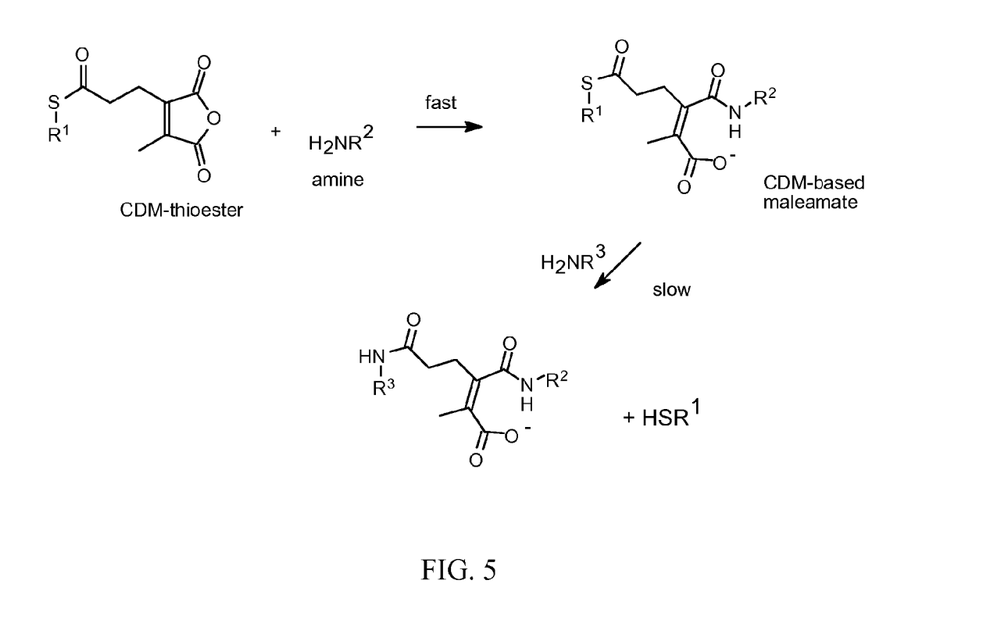
FIG. 5. Illustration of pH labile crosslinking of two amine-containing molecules using CDM-thioester.

Increased Particle Stability by Covalent Attachment Between Polymers:

In addition to the stability of particles due to the electrostatic forces between polycation and polyanion, the stability of the particle may also be enhanced by the formation of the covalent bonds, i.e. crossslinking, between the polymers. However, irreversible crosslinking of the polycation and polyanion results in particles that are ineffective for delivery of biologically active nucleic acids. In order to give the particles the stability of crosslinking while still providing the particles with intracellular instability, the polycation and polyanion of a nanoparticle can covalently linked via a plurality of acid labile maleamate bonds. In order to couple a CDM-based polyanion with a polyamine, it is necessary to use a crosslinking group that can react with amines only after the anhydride has reacted to form the CDM-based maleamate group. This selectivity in reaction is required because both formation of the maleamate and crosslinking between polyanion and polycation involve reactions with amines. As a consequence, in order to selectively couple a CDM-based polyanion and polyamine, there must be selectivity of the amine reactions. A method to accomplish this selectivity is to provide, on a CDM derivative, a functional group for crosslinking that is less reactive than the anhydride group involved in maleamate formation. Such a functional group is a thioester. A thioester is moderately amine-reactive relative to an anhydride. Using a thioester derivative of CDM, it is possible to link two amines together via a pH-labile maleamate bond (FIG. 5).

In addition to the maleamate bond, other pH labile bonds may be incorporated into crosslinking reagents including acetals, enol ethers, and hydrazones. In particular, acetals derived from benzaldehyde and benzaldehyde derivatives are very pH labile.

Figure 6:
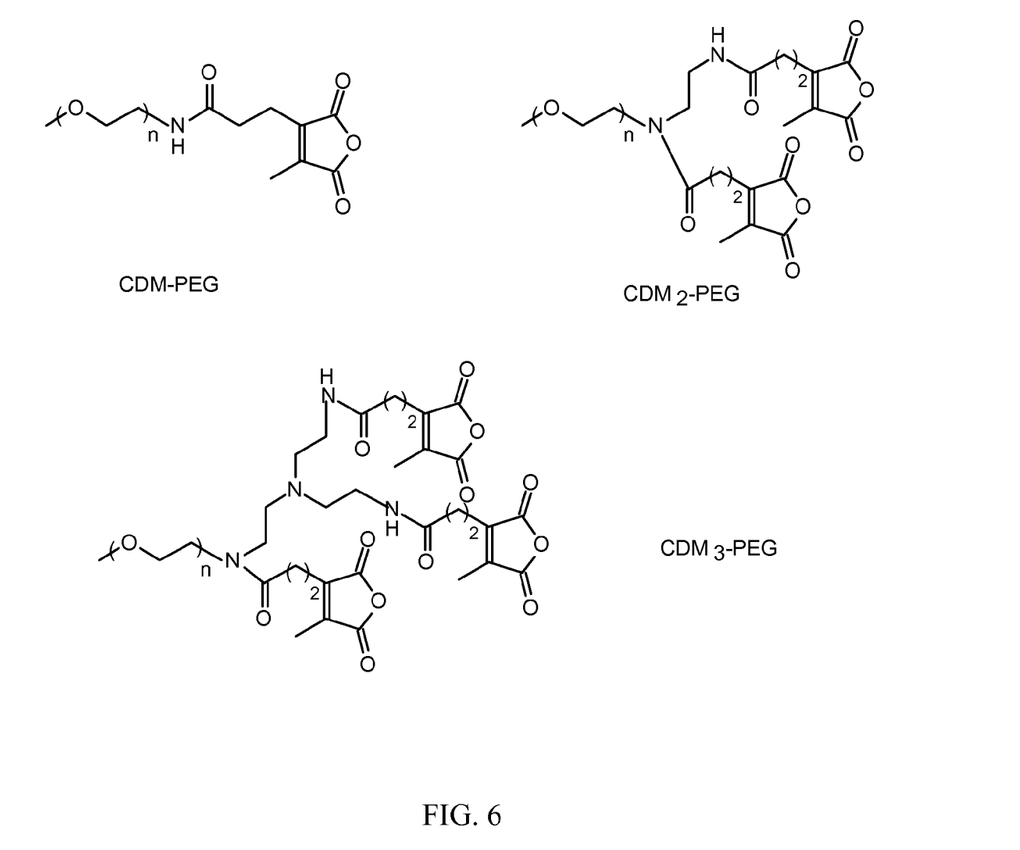
FIG. 6. Illustrations of the chemical structures for CDM-PEG, $CDM_2$-PEG, and $CDM_3$-PEG.

Increased Particle Stability by Covalent Attachment of Polyethyleneglycol:

In addition to increasing stability in the presence of salt, targeting of particles in vivo requires that nonspecific interactions, with serum component and non-targeted cells, be reduced. In order to reduce such interactions with delivery vehicles, many researchers have attached polyethylene glycol (PEG) (Kircheis et al. 2001; Woodle et al. 1992), an uncharged water-soluble polymer, to nucleic acid containing particles. However, PEG also decreases the transfection competency of particles. In order to gain the benefits of PEGylation while maintaining transfection ability, we have synthesized a variety of dimethylmaleic anhydride-derived PEGylation reagents. Attachment of a plurality of dimethylmaleic anhydride groups to a single PEG group allows for the formation of a plurality of reversible covalent bonds with the particle thereby increasing the stability of a particle (FIG. 6). A plurality of PEG groups can be covalently attached to a particle.

Membrane active—Membrane active polymers or compounds are molecules that are able to alter membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release.

Polymer—A polymer is a molecule built up by repetitive bonding together of smaller units called monomers. A polymer can be linear, branched network, star, comb, or ladder types of polymer. A polymer can be a homopolymer in which a single monomer is used or can be copolymer in which two or more monomers are used.

The main chain of a polymer is composed of the atoms whose bonds are required for propagation of polymer length. For example in poly-L-lysine, the carbonyl carbon, $\alpha$-carbon, and $\alpha$-amine groups are required for the length of the polymer and are therefore main chain atoms. The side chain of a polymer is composed of the atoms whose bonds are not required for propagation of polymer length. For example in poly-L-lysine, the $\beta$, $\gamma$, $\delta$ and $\in$-carbons, an $\in$-nitrogen are not required for the propagation of the polymer and are therefore side chain atoms.

Polycation—A polycation can be a polymer possessing net positive charge, for example poly-L-lysine hydrobromide or a histone. The polymeric polycation can contain monomer units that are charge positive, charge neutral, or charge negative, however, the net charge of the polymer must be positive. A polycation also can be a non-polymeric molecule that contains two or more positive charges.

Polyanion—A polyanion can be a polymer containing a net negative charge, for example polyglutamic acid. The polymeric polyanion can contain monomer units that are charge negative, charge neutral, or charge positive, however, the net charge on the polymer must be negative. A polyanion can also be a non-polymeric molecule that contains two or more negative charges.

Other Components of the Monomers and Polymers: Polymers may have functional groups that enhance their utility. These groups can be incorporated into monomers prior to polymer formation or attached to the polymer after its formation. Functional groups may be selected from the list consisting of: targeting groups, interaction modifiers, steric stabilizers, and membrane active compounds, affinity groups and reactive groups.

Targeting groups—Targeting groups, or ligands, are used for targeting the polymer or polymer complex to cells, to specific cells, to tissues or to specific locations in a cell. Targeting groups enhance the association of molecules with a cell. Examples of targeting groups include those that target to the asialoglycoprotein receptor by using asialoglycoproteins or galactose residues. Other proteins such as insulin, EGF, or transferrin can be used for targeting. Other targeting groups include molecules that interact with membranes such as fatty acids, cholesterol, dansyl compounds, and amphotericin derivatives. A variety of ligands have been used to target drugs and genes to cells and to specific cellular receptors. The ligand may seek a target within the cell membrane, on the cell membrane or near a cell. Binding of a ligand to a receptor may initiate endocytosis.

Steric stabilizer—A steric stabilizer is a long chain hydrophilic group that prevents aggregation of final polymer by sterically hindering particle to particle electrostatic interactions. Examples include: alkyl groups, PEG chains, polysaccharides, hydrogen molecules, alkyl amines.

Interaction modifier—An interaction modifier changes the way that a molecule interacts with itself or other molecules, relative to molecule containing no interaction modifier. The result of this modification is that self-interactions or interactions with other molecules are either increased or decreased. For example cell targeting signals are interaction modifiers with change the interaction between a molecule and a cell or cellular component. Polyethylene glycol is an interaction modifier that decreases interactions between molecules and themselves and with other molecules.

A labile linkage is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative. pH-labile refers to the selective breakage of a covalent bond under acidic conditions (pH<7). That is, the pH-labile bond may be broken under acidic conditions in the presence of other covalent bonds without their breakage. The term pH-labile includes both linkages and bonds that are pH-labile, very pH-labile, and extremely pH-labile. pH-labile refers to the selective breakage of a covalent bond under acidic conditions (pH<7). A pH-labile bond may be broken under acidic conditions in the presence of other covalent bonds without their breakage. For the purposes of the present invention, a bond is considered very pH-labile if the half-life for cleavage at pH 5 is less than 45 minutes. For the purposes of the present invention, a bond is considered extremely pH-labile if the half-life for cleavage at pH 5 is less than 15 minutes.

Targeting Groups—Targeting groups, or ligands, are used for targeting the polymer or polymer complex to cells, to specific cells, to tissues or to specific locations in a cell. Targeting groups enhance the association of molecules with a cell. Examples of targeting groups include those that target to the asialoglycoprotein receptor by using asialoglycoproteins or galactose residues. Other proteins such as insulin, EGF, or transferrin can be used for targeting. Other targeting groups include molecules that interact with membranes such as fatty acids, cholesterol, dansyl compounds, and amphotericin derivatives. A variety of ligands have been used to target drugs and genes to cells and to specific cellular receptors. The ligand may seek a target within the cell membrane, on the cell membrane or near a cell. Binding of a ligand to a receptor may initiate endocytosis.

Polynucleotide—The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA.

The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (mRNAs) are small noncoding polynucleotides, about 22 nucleotides long, that direct destruction or translational repression of their mRNA targets. Antisense polynucleotides comprise sequence that is complimentary to an gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Transfection—The process of delivering a polynucleotide to a cell has been commonly termed transfection or the process of transfecting and also it has been termed transformation. The term transfecting as used herein refers to the introduction of a polynucleotide or other biologically active compound into cells. The polynucleotide may be used for research purposes or to produce a change in a cell that can be therapeutic. The delivery of a polynucleotide can lead to modification of the genetic material present in the target cell. A transfection reagent or delivery vehicle is a compound or compounds that bind(s) to or complex(es) with oligonucleotides and polynucleotides, and mediates their entry into cells.

Application Ser. Nos. 10/619,778 and 10/816,081 are incorporated herein by reference.

EXAMPLES

Example 1

Synthesis of 2-propionic-3-methylmaleic anhydride (carboxydimethylmaleic anhydride or CDM).

To a suspension of sodium hydride (0.58 g, 25 mmol) in 50 mL anhydrous tetrahydrofuran was added triethyl-2-phosphonopropionate (7.1 g, 30 mmol). After evolution of hydrogen gas had stopped, dimethyl-2-oxoglutarate (3.5 g, 20 mmol) in 10 mL anhydrous tetrahydrofuran was added and stirred for 30 minutes. Water, 10 mL, was then added and the tetrahydrofuran was removed by rotary evaporation. The resulting solid and water mixture was extracted with 3×50 mL ethyl ether. The ether extractions were combined, dried with magnesium sulfate, and concentrated to a light yellow oil. The oil was purified by silica gel chromatography elution with 2:1 ether:hexane to yield 4 g (82% yield) of pure triester. The 2-propionic-3-methylmaleic anhydride was then formed by dissolving of this triester into 50 mL of a 50/50 mixture of water and ethanol containing 4.5 g (5 equivalents) of potassium hydroxide. This solution was heated to reflux for 1 hour. The ethanol was then removed by rotary evaporation and the solution was acidified to pH 2 with hydrochloric acid. This aqueous solution was then extracted with 200 mL ethyl acetate, which was isolated, dried with magnesium sulfate, and concentrated to a white solid. This solid was then recrystallized from dichloromethane and hexane to yield 2 g (80% yield) of 2-propionic-3-methylmaleic anhydride.

Example 2

Synthesis of CDM thioester.

To a solution of 2-propionic-3-methylmaleic anhydride (30 mg, 0.16 mmol) in 5 mL methylene chloride was added oxalyl chloride (200 mg, 10 eq) and dimethylformamide (1 µL). The reaction was allowed to proceed overnight at which time the excess oxalyl chloride and methylene chloride were removed by rotary evaporation to yield the acid chloride, a clear oil. The acid chloride was dissolved in 1 mL of methylene chloride. To this solution was added 2 equivalents thioglycolic acid, and pyridine (20 µL, 1.5 eq) in 10 mL of methylene chloride. The solution was then stirred overnight. The solvent was then removed and the resulting solid was dissolved into 5 mL of water and purified using reverse-phase HPLC using a 0.1% TFA water/acetonitrile gradient.

Example 3

Synthesis of Polyvinylethers.

2-Vinyloxy Ethyl Phathalimide (1 g, 4.6 mmol) was added to a oven dried round bottom flask under a blanket of nitrogen in anhydrous dichloromethane to this solution was added ethyl vinyl ether (0.332 g, 4.6 mmol), propyl vinyl ether (0.396 g, 4.6 mmol) or butyl vinyl ether (0.460 g, 4.6 mmol). These solutions were then brought to −78° C. and $BF_3.OEt_2$ (0.065 g, 0.46 mmol) is added and the reaction is allowed to proceed for 2 hours at −78° C. The polymerization is then stopped by the addition of 50/50 mixture of ammonium hydroxide in methanol. The solvents are then removed by rotary evaporation. The polymer is then dissolved in 30 mL of 1,4-dioxane/methanol (2/1). To this solution was added hydrazine (0.147 g, 46 mmol) and the mixture was heated to reflux for 3 hours. The solvents are then removed by rotary evaporation and the resulting solid was then brought up in 20 mL of 0.5M HCl and refluxed for 15 minutes, diluted with 20 mL distilled water, and refluxed for additional hour. This solution was then neutralized with NaOH cooled to room temperature and transfer to 3,500 molecular cellulose tubing and dialyzed for 24 h (2×20 L) against distilled water, and freeze dried.

Example 4

Hemolysis by melittin, PEAVE, PPAVE, PBAVE, and CDM-modified PBAVE.

The membrane activity of the amphiphilic cation polymers was tested according to published procedure. $10^8$ red blood cells were added to 500 µL of phosphate buffer. To this solution was added 20 µg of melittin, PEAVE, PPAVE, PBAVE, or CDM-PBAVE, which was made by acylation of PBAVE with 2 eq. of CDM relative to amines. The samples were incubated for 15 min at 37° C., then spun for 1 min at 15,000 RCF. Lysis was be determined by measuring the absorbance of the supernatant at 541 nm. Percent hemolysis was calculated assuming 100% lysis to be the absorbance of hemoglobin released upon addition of deionized water. All of the polymers were determined to be hemolytic, with PBAVE and melittin being the most lytic. CDM-modified polymer PBAVE was not hemolytic until acidification.

Example 5

Induction of luciferase upon delivery of oligonucleotide.

HeLa Luc/705 cells (Gene Tools, Philomath Oreg.) were grown under conditions used for HeLa cells. The cells were plated in 24-well culture dishes at a density of $3 \times 10^6$ cells/well and incubated for 24 hours. Media was replaced with 1.0 ml DMEM containing 10% fetal bovine serum and 2.5 nmol PMO (CCT CTT ACC TCA GTT ACA ATT TAT A, SEQ ID 1, Gene Tools, Philomath, Oreg.) either with or without 20 µg of CDM-modified PBAVE. The cells were then incubated for 48 hours in a humidified, 5% $CO_2$ incubator at 37° C. The cells were harvested and the lysates assayed for luciferase expression using a Lumat LB 9507 (EG&G Berthold, Bad-Wildbad, Germany) luminometer. Addition of CDM-modified PBAVE resulted in a 2-3 fold increase in luciferase activity.

Example 6

Transfection with Acid-Labile DNA Particles:

Hepa cells (a mouse hepatocyte cell line) were cultured in 1 mL Dulbecco's modified Eagle Media containing 10% fetal bovine serum using 12-well plates. PBAVE nanoparticles were formulated according the reported ratios with plasmid DNA pCIluc (10 µg/mL, pCIluc; prepared according to published procedure in 0.5 mL of 5 mM HEPES pH 7.5. As controls for the pH-labile CDM modification, polyanions were generated from the polyamines using succinic anhydride, which irreversibly modifies the amine, and aconitic anhydride, which reversibly modifies the amine but is much slower to cleave than CDM, to form S-PBAVE and A-PBAVE respectively. The nanoparticles, 2 µg of DNA, were then added (200 µL) to the cells. The cells were incubated for 48 h. The cells were harvested and assayed for luciferase expression as previously reported. A Lumat LB 9507 (EG&G Berthold, Bad-Wildbad, Germany) luminometer was used. The amount of transfection is average transfection for two separate wells of cells. Amount of luciferase in picograms=$5.1 \times 10^{-5}$(RLU)+3.683.

| Formulation | Relative Light Units |
|---|---|
| DNA:PBVE:CDM-PBAVE 10:20:80 µg/mL | 1,875,801 |
| DNA:PBVE:S-PBAVE 10:20:80 µg/mL | 195 |
| DNA:PBVE:A-PBAVE 10:20:80 µg/mL | 68,549 |
| Naked DNA | 200 |

Example 7

Transfection with Recharged acid-labile particles in vivo.

PBAVE nanoparticles were formulated according the reported ratios with plasmid DNA pCIluc (30 µg/mL, pCIluc; prepared according to published procedure in 0.5 mL of 5 mM HEPES pH 7.5. The nanoparticles, 9 µg of DNA, were then injected into the tail vein (300 µL) of mice. 24 hours postinjection, the mice were sacrificed, their livers harvested and assayed for luciferase expression as previously reported. A Lumat LB 9507 (EG&G Berthold, Bad-Wildbad, Germany) luminometer was used. The amount of transfection is average transfection for a group of three mice. Amount of luciferase in picograms=$5.1 \times 10^{-5}$(RLU)+3.683.

| Formulation | Relative Light Units |
| --- | --- |
| DNA:PBVE:CDM-PBAVE 30:60:240 µg/mL | 30,123 |
| Naked DNA | 1,021 |

Example 8

Particle Sizing in the Absence and Presence of Salt and ζ-Potential Measurement.

Nanoparticles between DNA and PEAVE and CDM/CDM-thioester-modified PEAVE were formulated in 20 mM HEPES buffer pH 7.5 according to the weight ratios presented above at a DNA concentration of 10 µg/mL. For the CDM/CDM-thioester modified polymers, CDM-thioester was mixed was CDM at a 9:1 weight ratio before mixing with the polymer. The size of the nanoparticles and the z-potential were determined by light scattering at 532 nm using a Brookhaven Instruments Corporation, ZetaPlus Particle Sizer, I90. The salt stability of the nanoparticles was assessed by addition of sodium chloride to 150 mM and measurement of size after 10 min.

| particles polymer wt. ratios (µg/mL) | Size (nm) in 20 mM HEPES pH 7.5 | Size (nm) in 150 mM NaCl |
| --- | --- | --- |
| DNA:PEAVE:CDM-PEAVE | | |
| 10:20:100 | 90-110 | >1000 |
| 5:10:100 | 90-130 | >1000 |
| DNA:PEAVE:CDM/CDMthioester-PEAVE | | |
| 10:20:100 | 90-110 | 114 |
| 5:10:100 | 90-130 | 118 |

Example 9

Transfection of CDM-Thioester Crosslinked DNA Particles.

Hepa cells (a mouse hepatocyte cell line) were cultured in 1 mL Dulbecco's modified Eagle Media containing 10% fetal bovine serum using 12-well plates. PBAVE nanoparticles were formulated according the reported ratios with plasmid DNA pCIluc (10 µg/mL, pCIluc; prepared according to published procedure in 0.5 mL of 5 mM HEPES pH 7.5. For the CDM/CDM-thioester modified polymers, CDM-thioester was mixed was CDM at a 9:1 weight ratio before mixing with the polymer. The nanoparticles, 2 µg of DNA, were then added (200 µL) to the cells. The cells were incubated for 48 h. The cells were harvested and assayed for luciferase expression as previously reported. A Lumat LB 9507 (EG&G Berthold, Bad-Wildbad, Germany) luminometer was used. The amount of transfection is average transfection for two separate wells of cells. Amount of luciferase in picograms=$5.1 \times 10^{-5}$(RLU)+3.683.

| Formulation | Relative light units (RLU) |
| --- | --- |
| DNA:PBAVE:CDM-PBAVE 10:40:100 µg/mL | 774,432 |
| DNA:PBAVE:CDM-PBAVE 10:20:50 µg/mL | 4,967,879 |
| DNA:PBAVE:CDM/CDM-thioester-PBAVE 10:40:100 µg/mL | 1,040,076 |
| DNA:PBAVE:CDM/CDM-thioester-PBAVE 10:20:50 µg/mL | 2,276,733 |

Example 10

Synthesis of amino polyethylene glycol monomethyl ethers.

To a 10 wt % solution of monomethyl ether PEG of various molecular weights in methylene chloride is added 3 equivalents of mesyl chloride and triethylamine. After stirring overnight, the solution is washed with an equal volume of NaHCO$_3$ saturated water. The organic layer is then dried with sodium sulfate and the PEG is precipitated out of solution by the addition of 9 volume equivalents of diethyl ether. The PEG mesylate is allowed to precipitate out overnight at −78° C. The PEG mesylate is then dissolved to 15 wt % in water and 10 equivalents of amine (ethylene diamine or Tris(2-aminoethyl)amine). The reaction is allowed to proceed for 48 hours and the amine-modified PEG is purified using reverse-phase HPLC using a 0.1% TFA water/acetonitrile gradient.

Example 11

Synthesis of CDM-PEG derivatives.

To a solution of 2-propionic-3-methylmaleic anhydride (30 mg, 0.16 mmol) in 5 mL methylene chloride was added oxalyl chloride (200 mg, 10 eq) and dimethylformamide (1 µL). The reaction was allowed to proceed overnight at which time the excess oxalyl chloride and methylene chloride were removed by rotary evaporation to yield the acid chloride, a clear oil. The acid chloride was dissolved in 1 mL of methylene chloride. To this solution was added 2 equivalents amino polyethylene glycol monomethyl ether of various molecular weights, and pyridine (20 µL, 1.5 eq) in 10 mL of methylene chloride. The solution was then stirred overnight. The solvent was then removed and the resulting solid was dissolved into 5 mL of water and purified using reverse-phase HPLC using a 0.1% TFA water/acetonitrile gradient.

Example 12

Particle Size in the Absence and Presence of Salt and ζ-Potential Measurement.

Nanoparticles between 10 µg/mL DNA and 20 µg/mL PBAVE were formulated in 20 mM HEPES buffer pH 7.5. To this solution was added nothing or 100 µg CDM-PEG$_2$ (the molecular weight of the PEG was 1100). The size of the nanoparticles and was determined by light scattering at 532 nm using a Brookhaven Instruments Corporation, ZetaPlus Particle Sizer, I90. The salt stability of the nanoparticles was assessed by addition of sodium chloride to 150 mM and measurement of size after 10 min. Without addition of CDM-PEG$_2$ the DNA/polycation particles grew from 100 to >1000 nm upon addition of sodium chloride. Upon modification with CDM-PEG2, this increase in particle size did not occur in the presence of salt.

Example 13

Condensation and decondensation of DNA upon addition of salt and polyacrylic acid.

DNA was labeled with tetramethylrhodamine LabelIT DNA labeling reagent (Mirus Corporation) at a 1:1 DNA:LabelIT weight ratio according to manufacturer's protocol. A solution of 1 μg/mL of tetramethylrhodamine-labeled DNA was condensed by the addition of 10 μg/mL of PBAVE in the presence of TAPS buffer pH 9. To this solution was added various amounts of $CDM\text{-}PEG_2$ and $CDM\text{-}PEG_3$. To the solution was then added NaCl bring the concentration to 150 mM. Finally polyacrylic acid was added to 100 μg/mL. After the addition of each reagent, the fluorescence of the rhodamine was measured using a Varian spectrofluorometer exciting at 555 nm and measure emission at 575 nm. A decrease in fluorescence is indicative of DNA condensation, while an increase indicates a decondensation of DNA.

| Sample | Fluorescence Relative |
|---|---|
| DNA alone | 1.0 |
| +PBAVE | 0.2 |
| +40 μg PEG(1100)-$CDM_2$ | 0.3 |
| +150 mM NaCl | 0.3 |
| +100 μg/mL PACAC | 0.75 |
| DNA alone | 1.0 |
| +PBAVE | 0.2 |
| +40 μg PEG(1100)-$CDM_3$ | 0.3 |
| +150 mM NaCl | 0.3 |
| +100 μg/mL PACAC | 0.79 |
| DNA alone | 1.0 |
| +PBAVE | 0.2 |
| +150 μg PEG(1100)-$CDM_3$ | 0.3 |
| +150 mM NaCl | 0.3 |
| +100 μg/mL PACAC | 0.56 |
| DNA alone | 1.0 |
| +PBAVE | 0.2 |
| +150 mM NaCl | 0.3 |
| +100 μg/mL PACAC | 0.95 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. An endosomolytic polymer made by the process comprising:
   a) forming a membrane active polyamine capable of disrupting a cell membrane, and
   b) reversibly modifying a plurality of amines on the polyamine by attachment of disubstituted maleic anhydrides having the structure:

to form a plurality of maleamates, thereby forming a polyanion that is not capable of disrupting red blood cells wherein cleavage of the maleamates from the polyanion regenerates the amines and restores cell membrane disruption activity of the polyamine.

2. The endosomolytic polymer of claim 1 wherein said membrane active polyamine has a molecular weight of at least 10,000 Daltons.